United States Patent [19]

Shoesmith, deceased

[11] Patent Number: Plant 5,945

[45] Date of Patent: Apr. 14, 1987

[54] CHRYSANTHEMUM PLANT NAMED CITADEL

[75] Inventor: Leonard H. Shoesmith, deceased, late of Westfield, England, by May Victoria Shoesmith, executrix

[73] Assignee: Ball Pan Am Plant Company, Parrish, Fla.

[21] Appl. No.: 747,066

[22] Filed: Jun. 20, 1985

[51] Int. Cl.[4] ..... A01H 5/00

[52] U.S. Cl. ..... Plt./76

[58] Field of Search ..... Plt./76

*Primary Examiner*—James R. Feyrer

*Attorney, Agent, or Firm*—Schwartz, Jeffery, Schwaab, Mack, Blumenthal & Evans

[57] ABSTRACT

A Chrysanthemum plant named Citadel having large flat capitulum form and quilled decorative capitulum type; medium lavender flower color which is a very pale white lavender under extreme high temperature; diameter across capitulum of 8 cm to 14 cm; vigorous growth habit and strong stems; and, uniform nine week flowering response.

1 Drawing Figure

The present invention comprises a new and distinct cultivar of *Chrysanthemum morifolium,* Ramat., hereinafter referred to by the cultivar name Citadel.

Citadel is a product of a planned breeding program which had the objective of creating new Chrysanthemum cultivars with decorative flowers in the purple-lavender color range, suitable for year around flowering in 6.5" pots. Such traits in combination were not present or needed improvement in previously available commercial cultivars.

Citadel was originated from a hybridization made in a controlled breeding program by Leonard H. Shoesmith in Westfield, Woking, Great Britain in 1978. The male and female parents are unknown at this time.

Citadel was discovered and selected as one flowering plant within the progeny of the stated parentage by or under the supervision of Leonard H. Shoesmith in November of 1979 in a controlled environment in West Chicago, Ill., and given the code #P9-1324-P.

The first act of asexual reproduction of Citadel was accomplished when vegetative cuttings were taken from the initial selection in February of 1980 in a controlled environment in West Chicago, Ill. by a technician working under formulations established and supervised by Leonard H. Shoesmith. Horticultural examination of selected units initiated February of 1980 has demonstrated that the combination of characteristics as herein disclosed for Citadel are firmly fixed and are retained through successive generations of asexual reproduction.

Citadel has not been observed under all possible environmental conditions. The phenotype may vary significantly with variations in environment such as temperature, light intensity and day length. The following observations, measurements and comparisons describe plants grown in West Chicago, Ill. and Parrish, Fla. under greenhouse conditions which approximate those generally used in commercial practice.

The following traits have been repeatedly observed and are determined to be basic characteristics of Citadel which in combination distinguish this chrysanthemum as a new and distinct cultivar:

(1) Large flat capitulum form.

(2) Quilled decorative type.

(3) Medium lavender color.

(4) Diameter across face of flower is 8 cm to 14 cm.

(5) Vigorous growth habit and strong stems.

(6) Uniform 9 week flowering response from October through June, using photoperiodic control.

(7) Height is 12" to 18" above edge of a 6" pot; height depends on the number of long days prior to bud initiation, maturity of the plants and temperature.

(8) Flower color is not well reproduced at high temperature, and under extremes will approximate a very pale white lavender.

Of the many commercial cultivars known to the present inventor, the most similar in comparison to Citadel is Tempo, disclosed in U.S. Plant Pat. No. 4,505. In comparison to Tempo, Citadel has a paler lavender color, and the ray florets are almost totally quilled. The vigor and response time are similar to those same characteristics of Tempo.

The accompanying photographic drawing shows typical inflorescence and foliage characteristics of Citadel. The photograph is in black and white except for a single flower, the color of which represents the true flower color of Citadel.

In the following description, color references are made to The Royal Horticultural Society Colour Chart. The color values were determined at approximately 12:00 noon on May 2, 1985 under inflorescent light at Bradenton, Fla.

Classification:

*Botanical.*—*Chrysanthemum morifolium,* Ramat., cv Citadel.

*Commercial.*—Disbud pot mum.

I. INFLORESCENCE

A. Capitulum:

*Form.*—Flat.

*Type.*—Quilled decorative.

*Diameter across face.*—8 cm to 14 cm.

B. Corolla of ray florets:

*Color (general tonality from a distance of three meters).*—Purple or lavender.

*Color (upper surface).*—77B–C; quilled tip, 77B.

*Color (under surface).*—77B–C.

C. Corolla of disc florets:

*Color (mature).*—Insignificant.

*Color (immature).*—Insignificant.

D. Reproductive organs:

*Androecium.*—None.
*Gynoecium.*—One per ray floret.

II. PLANT

A. General appearance:
*Height.*—12" to 18" above the edge of a 6" pot.
B. Foliage:
*Color (upper surface).*—147A.
*Color (under surface).*—147B.
*Shape.*—Deeply lobed.

It is claimed:

1. A new and distinct cultivar of Chrysanthemum plant named Citadel, as described and illustrated, and particularly characterized by its large flat capitulum form and quilled decorative capitulum type; medium lavender flower color which is a very pale white lavender under extreme high temperature; diameter across capitulum of 8 cm to 14 cm; vigorous growth habit and strong stems; and, uniform nine week flowering response.

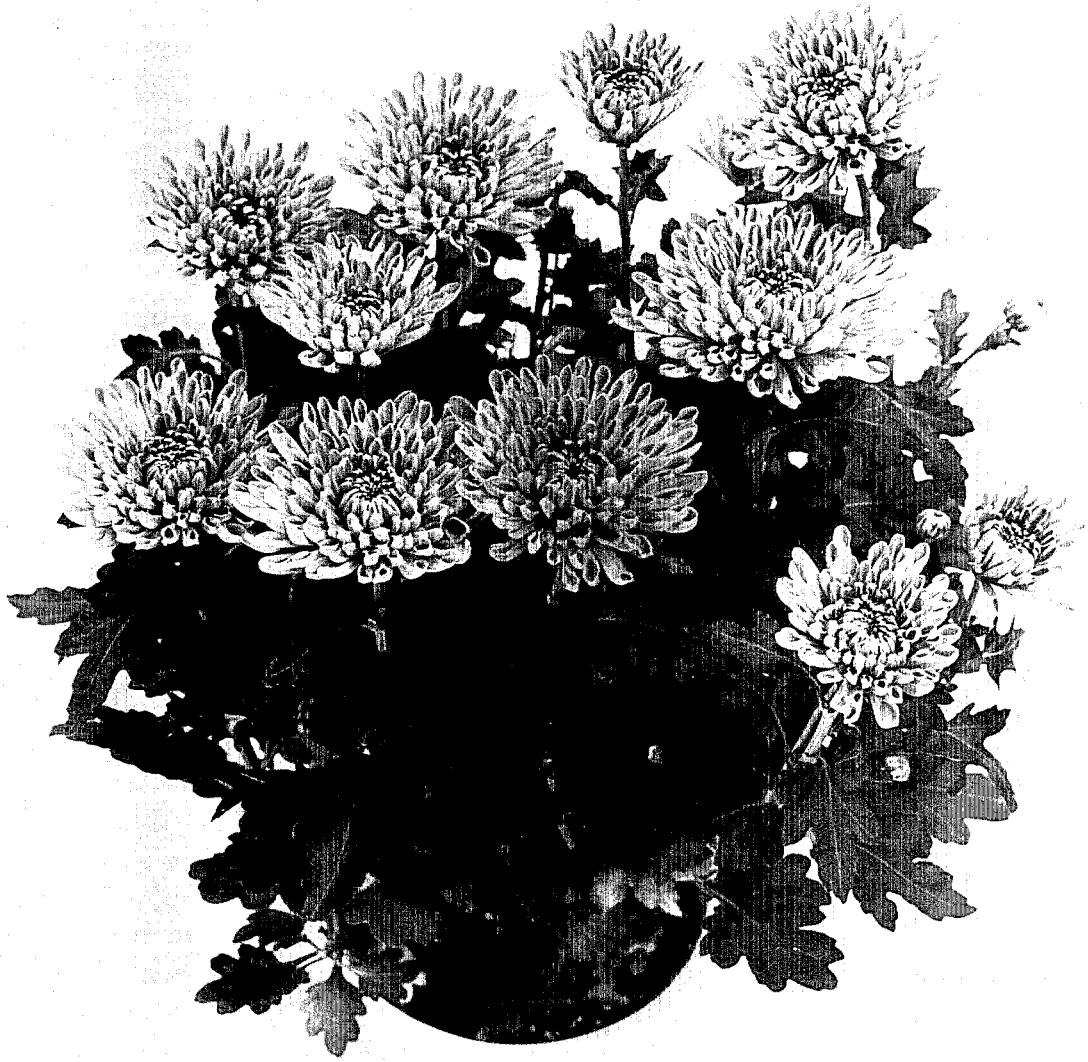

* * * * *